United States Patent
Bik et al.

(10) Patent No.: US 11,622,557 B2
(45) Date of Patent: Apr. 11, 2023

(54) DISPENSING OF METAL IONS INTO BATCH LAUNDRY WASHERS AND DRYERS

(71) Applicant: Applied Silver, Inc., Hayward, CA (US)

(72) Inventors: Russell J. Bik, Arroyo Grande, CA (US); James Charles Copeland, Arroyo Grande, CA (US); Elizabeth Hutt Pollard, Edmond, OK (US); William Morris, San Francisco, CA (US)

(73) Assignee: Applied Silver, Inc., Hayward, CA (US)

(*) Notice: Subject to any disclaimer, the term of this patent is extended or adjusted under 35 U.S.C. 154(b) by 12 days.

(21) Appl. No.: 16/348,988

(22) PCT Filed: Oct. 31, 2017

(86) PCT No.: PCT/US2017/059196
§ 371 (c)(1),
(2) Date: May 10, 2019

(87) PCT Pub. No.: WO2018/081774
PCT Pub. Date: May 3, 2018

(65) Prior Publication Data
US 2019/0281821 A1    Sep. 19, 2019

Related U.S. Application Data

(60) Provisional application No. 62/486,521, filed on Apr. 18, 2017, provisional application No. 62/486,523, filed on Apr. 18, 2017, provisional application No. 62/415,233, filed on Oct. 31, 2016.

(51) Int. Cl.
| | |
|---|---|
| *A01N 25/34* | (2006.01) |
| *A01N 25/04* | (2006.01) |
| *A01N 59/16* | (2006.01) |
| *A01N 59/20* | (2006.01) |
| *D06M 11/83* | (2006.01) |
| *A01N 25/12* | (2006.01) |
| *A61K 33/16* | (2006.01) |
| *A61K 33/34* | (2006.01) |
| *A61K 33/38* | (2006.01) |
| *A61L 2/238* | (2006.01) |

(52) U.S. Cl.
CPC .......... *A01N 25/34* (2013.01); *A01N 25/04* (2013.01); *A01N 25/12* (2013.01); *A01N 59/16* (2013.01); *A01N 59/20* (2013.01); *A61K 33/16* (2013.01); *A61K 33/34* (2013.01); *A61K 33/38* (2013.01); *D06M 11/83* (2013.01); *A61L 2/238* (2013.01); *A61L 2202/17* (2013.01); *A61L 2202/26* (2013.01)

(58) Field of Classification Search
CPC ....... D06M 11/83; A61K 33/16; A61K 33/34; A61K 33/38; A61L 2/238; A61L 2202/17; A61L 2202/26; A01N 25/24; A01N 25/04; A01N 25/12; A01N 59/16; A01N 59/20

See application file for complete search history.

(56) References Cited

U.S. PATENT DOCUMENTS

| | | |
|---|---|---|
| 4,710,282 A | 12/1987 | Chak et al. |
| 4,755,268 A | 7/1988 | Matsuo et al. |
| 5,202,045 A * | 4/1993 | Karpusiewicz ...... C11D 17/046 206/484 |
| 5,632,904 A | 5/1997 | Samad et al. |
| 6,037,319 A | 3/2000 | Dickler et al. |
| 6,136,776 A | 10/2000 | Dickler et al. |
| 6,294,186 B1 | 9/2001 | Beerse et al. |
| 6,303,039 B1 | 10/2001 | Back et al. |
| 6,448,212 B1 | 9/2002 | Holderbaum et al. |
| 6,468,950 B1 | 10/2002 | Kawasaki et al. |
| 6,555,098 B1 * | 4/2003 | Murphy ................ A61K 8/19 424/722 |
| 6,583,176 B2 | 6/2003 | Arata |
| 6,624,130 B2 | 9/2003 | Giblin et al. |
| 6,641,829 B1 | 11/2003 | Green et al. |
| 6,699,826 B1 | 3/2004 | Saijo et al. |
| 6,730,648 B2 | 5/2004 | Gorlin et al. |
| 6,736,936 B1 | 5/2004 | Weston et al. |
| 6,762,157 B1 | 7/2004 | Babinski et al. |

(Continued)

FOREIGN PATENT DOCUMENTS

| | | |
|---|---|---|
| CA | 162326 S | 1/2016 |
| CN | 1434729 A | 8/2003 |

(Continued)

OTHER PUBLICATIONS

Ngoc Duong Trinh et al. Preparation and characterization of silver chloride nanoparticles as an antibacterial agent. Adv. Nat. Sci: Nanosci. Nanotechnol. 6 045011, Nov. 13, 2015.*
Swicofil, Magic Blue Ball, http://web.archive.org/web/20071028122117/http://www.swicofil.com/bluemagicball_presentation_english.pdf, Oct. 28, 2007.

(Continued)

*Primary Examiner* — Amina S Khan
(74) *Attorney, Agent, or Firm* — McDonnell, Boehnen, Hulbert & Berghoff LLP

(57) ABSTRACT

Articles, compositions, and methods for treating textiles and other materials with an antimicrobial compound during laundry and/or drying cycles are described. The articles and compositions include a metal ion having antimicrobial efficacy. Methods include the use of the articles and compositions in laundry and/or drying cycles to provide antimicrobial treatment of the textiles and materials.

9 Claims, No Drawings

(56) References Cited

U.S. PATENT DOCUMENTS

| | | | |
|---|---|---|---|
| 6,838,095 B2 | 1/2005 | Newman et al. | |
| 6,927,201 B2 | 8/2005 | Hsu et al. | |
| 6,946,433 B2 | 9/2005 | Green et al. | |
| 6,958,313 B2 | 10/2005 | Caswell et al. | |
| 7,012,053 B1 | 3/2006 | Barnabas et al. | |
| 7,105,478 B2 | 9/2006 | Guzmann et al. | |
| 7,220,715 B2 | 5/2007 | Ghosh et al. | |
| 7,322,065 B2 | 1/2008 | Kim et al. | |
| 7,351,683 B2 | 4/2008 | Del Duca et al. | |
| 7,375,070 B2 | 5/2008 | Pegelow et al. | |
| 7,422,759 B2 | 9/2008 | Kepner et al. | |
| 7,481,081 B2 | 1/2009 | Hsu et al. | |
| 7,511,007 B2 | 3/2009 | Tichy et al. | |
| 7,517,846 B2 | 4/2009 | Gladfelter et al. | |
| 7,543,707 B2 | 6/2009 | Miller | |
| 7,617,704 B2 | 11/2009 | Iimori et al. | |
| 7,624,601 B2 | 12/2009 | Ikemizu et al. | |
| 7,638,476 B2 | 12/2009 | Orlich et al. | |
| 7,708,896 B2 | 5/2010 | Ooe et al. | |
| 7,718,596 B2 | 5/2010 | Briggs et al. | |
| 7,763,579 B2 | 7/2010 | Briggs et al. | |
| 7,819,127 B1 | 10/2010 | Huffman | |
| 7,927,379 B2 | 4/2011 | Cottrell et al. | |
| 8,003,589 B2 | 9/2011 | Panandiker et al. | |
| 8,163,690 B2 | 4/2012 | Brown et al. | |
| 8,173,067 B2 | 5/2012 | Eldred | |
| 8,232,238 B2 | 7/2012 | Ochomogo et al. | |
| 8,239,990 B2 | 8/2012 | Lim et al. | |
| 8,309,506 B2 | 11/2012 | Sunder et al. | |
| 8,394,420 B2 | 3/2013 | Kepner et al. | |
| 8,449,732 B2 | 5/2013 | Choi | |
| 8,460,395 B2 | 6/2013 | Smulowitz et al. | |
| 8,476,216 B2 | 7/2013 | Fernandes | |
| 8,551,933 B2 | 10/2013 | Parrish et al. | |
| 8,563,447 B2 | 10/2013 | Canada et al. | |
| 8,664,174 B2 | 3/2014 | Braeckman et al. | |
| 8,729,008 B2 | 5/2014 | Begli et al. | |
| 8,754,022 B2 | 6/2014 | Zhang et al. | |
| 8,815,786 B2 | 8/2014 | Meine et al. | |
| 8,809,250 B2 | 9/2014 | Parrish et al. | |
| 8,980,816 B2 | 3/2015 | Dreher et al. | |
| 9,121,000 B2 | 9/2015 | Burkinshaw et al. | |
| 9,132,296 B2 | 9/2015 | Wingfield | |
| 9,222,059 B2 | 12/2015 | Germain et al. | |
| 9,234,163 B2 | 1/2016 | Miracle | |
| 9,253,986 B2 | 2/2016 | King | |
| 2002/0023304 A1 | 2/2002 | Chan | |
| 2002/0189954 A1 | 12/2002 | Miyazaki et al. | |
| 2003/0104969 A1* | 6/2003 | Caswell | C11D 3/0021 510/513 |
| 2003/0118664 A1* | 6/2003 | Trogolo | C08K 9/08 424/641 |
| 2005/0188731 A1 | 9/2005 | Aouad | |
| 2006/0051430 A1* | 3/2006 | Arata | A61Q 19/00 424/618 |
| 2006/0068024 A1 | 3/2006 | Schroeder et al. | |
| 2006/0123556 A1 | 6/2006 | Caswell et al. | |
| 2006/0123562 A1 | 6/2006 | Ghosh et al. | |
| 2006/0233889 A1 | 10/2006 | Burton et al. | |
| 2007/0163097 A1 | 7/2007 | Metcalfe et al. | |
| 2007/0175833 A1 | 9/2007 | Ikeboh et al. | |
| 2008/0041117 A1 | 2/2008 | Lee | |
| 2008/0131471 A1 | 6/2008 | Kolbe et al. | |
| 2008/0147019 A1 | 6/2008 | Song et al. | |
| 2008/0256719 A1 | 10/2008 | Radev | |
| 2009/0000040 A1 | 1/2009 | Ikemizu | |
| 2009/0035342 A1 | 2/2009 | Karandikar et al. | |
| 2009/0218266 A1 | 9/2009 | Sawafta et al. | |
| 2010/0000268 A1 | 1/2010 | Kohne | |
| 2010/0116689 A1 | 5/2010 | Greene | |
| 2011/0100838 A1 | 5/2011 | Kim et al. | |
| 2011/0200674 A1 | 9/2011 | MacKay | |
| 2012/0003326 A1 | 1/2012 | Meine | |
| 2012/0192363 A1 | 9/2012 | King | |
| 2014/0202943 A1 | 7/2014 | Pradeep et al. | |
| 2014/0274859 A1 | 9/2014 | Adamy | |
| 2014/0369953 A1* | 12/2014 | Purschwitz | A01N 31/16 424/78.36 |
| 2015/0175724 A1* | 6/2015 | Klostermann | C08K 3/36 514/772.3 |
| 2015/0330020 A1* | 11/2015 | van Buskirk | A01N 25/34 424/618 |
| 2015/0376550 A1 | 12/2015 | Ohtani et al. | |
| 2016/0010041 A1 | 1/2016 | Sivik et al. | |
| 2016/0040104 A1 | 2/2016 | Liu et al. | |
| 2016/0083900 A1 | 3/2016 | Johnson | |
| 2016/0281032 A1 | 9/2016 | Vockenroth et al. | |
| 2016/0287741 A1* | 10/2016 | Harris | A61L 15/56 |
| 2016/0340625 A1 | 11/2016 | Scheibel et al. | |
| 2021/0237035 A1* | 8/2021 | Gomes | B01J 20/043 |

FOREIGN PATENT DOCUMENTS

| | | | | |
|---|---|---|---|---|
| CN | 2753774 Y | 1/2006 | | |
| CN | 2780804 Y | 5/2006 | | |
| CN | 101307555 B | 11/2008 | | |
| CN | 101646820 A | 2/2010 | | |
| CN | 1671911 B | 6/2010 | | |
| CN | 101926363 B | 12/2010 | | |
| CN | 201738163 U | 2/2011 | | |
| CN | 101991870 B | 3/2011 | | |
| CN | 201791121 U | 4/2011 | | |
| CN | 102165960 A | 8/2011 | | |
| CN | 202021117 U | 11/2011 | | |
| CN | 202036069 U | 11/2011 | | |
| CN | 102395608 A | 3/2012 | | |
| CN | 102535114 A | 7/2012 | | |
| CN | 202386643 U | 8/2012 | | |
| CN | 202430491 U | 9/2012 | | |
| CN | 101010004 B | 10/2012 | | |
| CN | 104245781 A | 12/2014 | | |
| EP | 1134012 A1 | 9/2001 | | |
| EP | 1276842 B1 | 1/2003 | | |
| EP | 1881058 A2 | 1/2008 | | |
| EP | 1927286 A1 | 6/2008 | | |
| EP | 2045389 A1 | 4/2009 | | |
| EP | 2631289 B1 | 8/2012 | | |
| EP | 2499916 A1 | 9/2012 | | |
| EP | 2674523 A2 | 12/2013 | | |
| GB | 2498877 A | 7/2013 | | |
| JP | H06297626 A | 4/1994 | | |
| JP | 2001062458 A | 3/2001 | | |
| JP | 2002113288 A | 4/2002 | | |
| JP | 2008183283 A | 8/2008 | | |
| JP | 2008279056 A | 11/2008 | | |
| KR | 20060096652 A | 9/2006 | | |
| KR | 10-2006-0117875 | * | 11/2006 | C11D 3/08 |
| RU | 2193528 C2 | 11/2002 | | |
| TW | I252268 B | 8/2004 | | |
| TW | 200902790 A | 1/2009 | | |
| TW | 201013008 A | 4/2010 | | |
| WO | 1999/039749 A2 | 8/1998 | | |
| WO | 2004/104153 A1 | 2/2004 | | |
| WO | WO2006049478 | * | 5/2006 | A01N 59/16 |
| WO | WO2006050477 A2 | 5/2006 | | |
| WO | 2006/129982 A1 | 12/2006 | | |
| WO | 2007/057077 A1 | 5/2007 | | |
| WO | WO2010002773 A2 | 1/2010 | | |
| WO | WO2010119022 | * | 10/2010 | C08F 8/28 |
| WO | 2012/031853 A1 | 8/2011 | | |
| WO | WO2011103046 A1 | 8/2011 | | |
| WO | 2012/095665 A2 | 7/2012 | | |
| WO | 2012/126786 A1 | 9/2012 | | |
| WO | 2012/142025 A1 | 10/2012 | | |
| WO | WO2016135344 A1 | 9/2016 | | |

OTHER PUBLICATIONS

International Search Report and Written Opinion for PCT/US2017/59196, 9 pages, dated Feb. 21, 2018.

"Antimicrobial AlphaSan RC 2000: Silver sodium hydrogen zirconium phosphate," Sep. 22, 2017 (Sep. 22, 2017), 1 page 1, XP55711339,

(56) References Cited

OTHER PUBLICATIONS

U.S.A., Retrieved from the Internet: URL:http://hawaii.gov/hdoa/labels/8171.3.pdf [retrieved on Jul. 2, 2020].

* cited by examiner

DISPENSING OF METAL IONS INTO BATCH LAUNDRY WASHERS AND DRYERS

CROSS REFERENCE TO RELATED APPLICATIONS

This application claims the benefit of priority of U.S. Provisional Patent Application No. 62/415,233, filed Oct. 31, 2016, U.S. Provisional Patent Application No. 62/486,521, filed Apr. 18, 2017, and U.S. Provisional Patent Application No. 62/486,523, filed Apr. 18, 2017, which are hereby incorporated by reference in their entirety.

FIELD

The disclosure relates to antimicrobial treatment of textiles and other materials. More particularly, the disclosure relates to compositions, articles, and methods for imparting metal ions into the wash and/or dry cycles of laundry systems for the purpose of antimicrobial treatment of the textiles and materials.

BACKGROUND

The microbial contamination of fabrics or linens used in clothing, bedsheets, towels, pillows, blankets and similar materials can contribute to staining of the textiles, unwanted odor, and the spread of disease. Previous methods of fabric treatment have included fabrics made of materials that contain or are coated with metals such as silver or copper to provide long-lasting antimicrobial protection. However, the antimicrobial efficacy of metalized fabrics declines with each laundering.

Accordingly, the inventors have identified a need in the art to provide products and methods that provide consistent anti-microbial efficacy for laundered articles.

SUMMARY

In one aspect, the disclosure is directed to a composition comprising a plurality of water-soluble particles comprising a metal salt comprising a metal ion having antimicrobial efficacy. The metal salt is enclosed by the particles or impregnated into the particles. The plurality comprises particles having one or more sizes, particles having one or more material compositions, and particles having one or more metal salt loadings. The metal ion may be a silver ion or a copper ion. The composition may be a liquid composition or a dry composition.

The composition may comprise a second salt comprising a counterion to the metal ion. The counterion may be selected from nitrate, fluoride, sulfate, carbonate, chloride, bromide, iodide, and sulfide.

In another aspect, the disclosure is directed to a water-in-oil emulsion. The water phase of the water-in-oil emulsion comprises a metal ion having antimicrobial efficacy. The emulsion can comprise amphiphilic Janus nanoparticles. The metal ion may be a silver ion or a copper ion. In some embodiments, an article comprises the water-in-oil emulsion and a water-soluble outer layer enclosing the composition. The water-soluble outer layer may comprise polyvinyl alcohol (PVA).

In another aspect, the disclosure is directed to an article comprising a sheet or strip impregnated with a metal salt comprising a metal ion having antimicrobial efficacy. The sheet or strip is coated with a water-soluble gel impregnated with a metal salt comprising a metal ion having antimicrobial efficacy. The strip or sheet may be folded, and the water-soluble gel may be coated onto the folded strip or sheet. The article may comprise a water-soluble outer layer. The article may comprise a metal salt comprising a metal ion having antimicrobial efficacy between the gel-coated strip and the outer layer. The metal ion may be a silver ion or a copper ion. The strip or sheet may be impregnated with a second salt comprising a counterion to the metal ion. The counterion may be selected from nitrate, fluoride, sulfate, carbonate, chloride, bromide, iodide, and sulfide. The water-soluble gel or water-soluble outer layer may comprise PVA.

In another aspect, the disclosure is directed to a method for introducing a metal ion to at least one of a wash cycle and a rinse cycle. The method includes dispensing, at or near the beginning of the wash cycle, a composition disclosed herein.

In another aspect, the disclosure is directed to a method for treating a textile. The method may include loading the textile into a wash basin containing water, and loading an article disclosed herein into the wash basin. The method may include washing the textile in a wash basin in the presence of an article disclosed herein, transferring the textile and the article from the wash basin to a dryer, and drying the textile in the presence of the article.

DESCRIPTION

The singular forms of the articles "a," "an," and "the" include plural references unless the context clearly indicates otherwise. For example, the term "a compound" or "at least one compound" can include a plurality of compounds, including mixtures thereof.

The disclosure relates to compositions and articles including a metal ion having antimicrobial efficacy. The compositions and articles can be added to a wash basin (i.e., of a conventional washer extractor) or to the drying cycle in a tumble drying machine to impart the metal ion to the textiles during the wash or drying cycles.

For instance, in a typical home use laundry and drying system, household textiles (clothes, sheets, towels, etc.) are laundered in conventional washer extractors and tumble drying machines. Soiled textiles are laundered in wash and rinse cycles in a washing machine and then are moved to the dryer to complete the process. An article or composition according to the disclosure can be added along with the soiled textiles directly into the washer, or an article may be added along with the clean, wet textiles to the dryer. In some instances, the article is added to the washer and then moved along with textiles into the dryer.

One aspect of the disclosure is a composition including a plurality of water-soluble particles comprising a metal salt comprising a metal ion having antimicrobial efficacy. In some embodiments, the metal salt is enclosed by the particles. In some embodiments, the metal salt is impregnated into the particles. In some embodiments, the particles of the composition have one or more sizes, one or more material compositions, and one or more metal salt loadings.

The particulate composition may be in dry form or liquid form, and either form may be enclosed or contained in another solid or semi-solid form (e.g., a laundry pod). In some embodiments, the composition includes water-soluble particles having a variety of sizes and/or materials that have varying dissolution profiles. The particles are impregnated with and/or enclose one or more metal salts that have antimicrobial efficacy. For example, in some embodiments, the metal salt comprises a silver ion (e.g., silver nitrate). In another example, in some embodiments, the metal salt comprises a copper ion. The counterion may be any metal salt counterion known in the art such as nitrate, sulfate, fluoride, carbonate, chloride, and the like. In some embodiments, the metal ion and counterion may comprise, e.g., silver sulfate, silver nitrate, silver chloride, copper sulfate, copper chloride, copper nitrate, etc.

In some embodiments, the particles are impregnated with or enclose one or more second salts that provide a counterion(s) to the metal ion(s) of the metal salt(s). For example, in some embodiments, the metal salt provides a counterion selected from nitrate, fluoride, sulfate (e.g. from sodium sulfate or potassium sulfate), carbonate (e.g. from sodium carbonate), chloride, bromide, iodide, and sulfide.

During one or both of the wash and the rinse cycle, which follows the wash cycle, the particles may dissolve in water in the wash basin, releasing metal ions into the wash water. The particles may be of various sizes and material compositions such that they will dissolve at different rates in the wash and rinse water, providing a timed release of the metal ions. In various embodiments, the particles may be formed from one or more polymers that may include polyvinyl alcohol (PVA), polyacrylamide, poly(acrylic acid), poly(dimethylaminoethylacrylate) (PDMEA), poly(dimethylacrylamide) (PDMA), polyethylene glycol (PEG), ethyl cellulose, gelatin, sodium alginate, or other water-soluble polymers that are readily removed from the wash basin as part of the wash and rinse cycles. The particles can range from about 1 mm, for fast release of silver ions, to about 25 mm, for slower release of silver ions. Larger sizes or thicknesses may take longer to dissolve, and may include two or more layers that dissolve at different rates for timed release of metal ions. The larger particles may have metal salts enclosed in their centers that will be released when the outer layers dissolve. In addition, most commercially available laundry machines will prevent larger particles from being discharged when water is emptied at the end of the wash cycle, which allows the particles to be available to release metal ions into the rinse cycle before they dissolve completely. Given the same amount of silver in a large particle and a small particle, the larger particle, impregnated with metal salts, will release metal ion at a slower rate.

Another aspect of the disclosure is a composition including a water-in-oil emulsion. In some embodiments, the water phase of the emulsion comprises a metal ion having antimicrobial efficacy. For example, in some embodiments, the metal salt comprises a silver ion (e.g., silver nitrate). In another example, in some embodiments, the metal salt comprises a copper ion. The counterion may be any metal salt counterion known in the art such as nitrate, sulfate, fluoride, carbonate, chloride, and the like. In some embodiments, the metal ion and counterion may comprise, e.g., silver sulfate, silver nitrate, silver chloride, copper sulfate, copper chloride, copper nitrate, etc. The water phase of the water-in-oil emulsion may further comprise one or more second salts that provide a counterion(s) to the metal ion(s) of the metal salt(s). For example, in some embodiments, the metal salt provides a counterion selected from nitrate, fluoride, sulfate (e.g. from sodium sulfate or potassium sulfate), carbonate (e.g. from sodium carbonate), chloride, bromide, iodide, and sulfide.

The oil of the water-in-oil emulsion in the composition may be any oil suitable for laundry. In some embodiments the oil is a hydrocarbon oil, for example, a paraffinic oil, a napthenic oil, natural mineral oil, and the like. In some embodiments, the oil is a silicone oil, for example, a polyalkyl siloxane, a polyaryl siloxane, or a poly alkylaryl siloxane, and the like. The emulsion may be prepared, for example, by sonication.

In some embodiments, the water-in-oil emulsion includes amphiphilic Janus particles, which may stabilize the emulsion. The Janus particles may comprise two domains, wherein one domain is hydrophilic and one domain is hydrophobic. In some embodiments, the Janus particle is polymeric. In one polymeric Janus particle example, the hydrophobic domain comprises polystyrene and the hydrophilic domain comprises poly(methyl methacrylate) (PMMA). The Janus particle may, for example, be a spherical particle comprising two hemispheres, wherein one hemisphere is hydrophilic and one hemisphere is hydrophobic. Alternatively, the Janus particle may be a dumbbell particle or ellipsoid particle. The Janus particle may be prepared according to methods known in the art such as, for example, phase separation.

In some embodiments, an article comprises the water-in-oil emulsion and a water-soluble outer layer enclosing the composition. The outer layer may comprise a water-soluble material such as, for example, polyvinyl alcohol (PVA), polyacrylamide, poly(acrylic acid), poly(dimethylaminoethylacrylate) (PMDEA), poly(dimethylacrylamide) (PDMA), polyethylene glycol (PEG), ethyl cellulose, gelatin, sodium alginate, or other water-soluble polymers. Sequestration of the metal-ion-containing water phase in the oil of the emulsion prevents degradation of the water-soluble material outer layer by the water phase. The article may have any number of different forms such as, for example, a sphere or pod.

The outer layer of the article may dissolve completely during the wash cycle or rinse cycle. Once dissolved, the water-in-oil emulsion contacts the water of the wash cycle or rinse cycle, releasing the metal ions of the water phase into the wash. The released metal ions may bind with fabric in the laundry. The time at which the outer layer is completely dissolved can be adjusted by the composition and/or the thickness of the water-soluble outer layer (i.e., to achieve a delayed release). In one embodiment, the composition comprises silver ions and the outer layer comprises PVA with a thickness such that the outer layer does not completely dissolve until after the wash cycle, releasing silver ions during a subsequent rinse cycle.

In one embodiment where the metal ion is silver, the water phase may be prepared by dissolving silver salt in the water phase.

Another aspect of the disclosure is an article comprising a sheet or strip impregnated with a metal salt comprising a metal ion having antimicrobial efficacy. In some embodiments, a water-soluble gel impregnated with a metal salt comprising a metal ion having antimicrobial efficacy is coated onto the sheet or strip.

The article can include a single-use porous sheet or strip that is dropped into the wash at the start of a load of laundry along with the clothes or other linens. The sheet or strip can have a number of different forms, and may be constructed from materials such as cotton, synthetic fiber, an open-cell foam plastic, or other porous material suitable for retaining and releasing the compounds described herein. In one embodiment, the sheet or strip of material may be impregnated with one or more metal salts (such as silver nitrate or copper salts) that have antimicrobial efficacy and, optionally, one or more second salts (such as sodium sulfate, sodium carbonate or potassium sulfate) that provide a counterion(s) to the metal ion(s) of the metal salt(s).

The sheet can be impregnated with the metal salts and optionally the second salt by, for example, (1) dipping the strip in a solution containing the salt(s), or (2) spraying the solution containing the salt(s) onto the sheets. After the dipping or spraying, the sheets are allowed to dry by conventional methods that may include the use of forced hot air.

Once dried, the impregnated strip or sheet may be coated with a water-soluble gel impregnated with one or more metal salts and second salts. The gel may dissolve completely during the wash cycle and part of the rinse cycle, releasing the metal salts into the wash on a gradual basis. When dissolved, the metal salts provide metal ions, such as silver or copper ions, to the wash basin that will bind with the fabric in the laundry. During the wash and rinse cycles, the impregnated sheet or strip will be exposed to the water in the wash basin and will release the metal ions into the wash water on a gradual basis. Therefore, the rate of dissolution of the salts can be adjusted by the composition of and/or the thickness of the gel coating. Examples of suitable gel coatings include polyvinyl alcohol (PVA), polyacrylamide, poly(acrylic acid), poly(dimethylaminoethylacrylate) (PDMEA), poly(dimethylacrylamide) (PDMA), polyethylene glycol (PEG), ethyl cellulose, gelatin, sodium alginate and other water-soluble polymers that are readily removed from the wash basin as part of the wash and rinse cycles.

The wet strip or sheet can be loaded into the dryer with the laundry, where it will mix with the laundry and transfer metal ions into the laundry during the dry cycle by direct contact with the wet laundry.

The metal-salt-impregnated sheet may also be folded to provide a smaller footprint before being coated with the water-soluble gel, which sheet will open to its full footprint when the gel coating dissolves in the wash and or rinse water. While the small, folded, footprint is desirable for packing and handling, the larger, unfolded footprint can make the metal-salt-impregnated sheet more effective when coming in contact with and transferring metal ions to wet clothing or fabrics in the dry cycle.

In another embodiment, the gel-coated sheet or strip impregnated with metal salts can be enclosed with a water-soluble outer layer, enclosing metal salts and possibly second salts between the outer layer and the gel-coated sheet or strip. Suitable materials for water-soluble films include polymers of polyvinyl alcohol (PVA), polyacrylamide, poly(acrylic acid), poly(dimethylaminoethylacrylate) (PDMEA), poly(dimethylacrylamide) (PDMA), polyethylene glycol (PEG), ethyl cellulose, gelatin, sodium alginate, and other water-soluble polymers that are readily removed from the wash basin as part of the wash and rinse cycles.

When the article comes into contact with the wash water, the outer layer will dissolve quickly, releasing the enclosed metal salts into the wash water. This will then expose the water-soluble gel and impregnated metal ions, which will release metal ions into the wash as it dissolves. When the gel coating dissolves it will expose the salt-impregnated sheet or strip, which will release metal ions into the wash and into the wet clothing or fabrics during the dry cycle.

Embodiments using the three-layer approach (i.e., including an impregnated sheet or strip, a water-soluble gel coating, and a water-soluble outer layer) provide a timed release of metal ions into the wash and rinse water to impregnate the laundry with metal ions and may also provide a method to deliver metal ions to the wet laundry in the dry cycle.

In a three-layer embodiment, the water-soluble outer layer may be composed of a thin, water-soluble film that can dissolve very quickly after contact with the water in the wash cycle. Upon dissolution of the outer later, the metal salts (which may be combined with binding or filler materials which will dilute or aid in achieving a timed release of ions into the wash) which were enclosed are released, allowing them to provide metal ions to fabrics in the wash. This will also expose the second layer, the water-soluble gel coating impregnated with metal salts, to the wash water. As the second layer dissolves, it will release the metal ions, which can then attach to the laundry fabrics and clothing. The second layer may not completely dissolve until after the completion of the wash cycle and the beginning of the rinse cycle so that the base layer (sheet or strip impregnated with silver and or copper salts) will be exposed and continue to release more ions into the wash cycle, the rinse cycle and ultimately the dry cycle, which will attach to the clothing and fabrics throughout the process. When dry, the depleted sheet or strip will be removed with the clothing and fabrics and discarded.

At the conclusion of the wash, the impregnated sheet or strip is removed along with the wet clothing or linens and moved to the dryer. In the dryer, a combination of water and metal ions will be on the surface of the sheet or strip, and capillary action will draw out all the water within the sheet or strip until it is dry. In the process, metal ions can adhere to the clothing or linens in the dryer through direct contact with the wet laundry The sheets or strips previously described can be wrapped with a paper or other protective covering which will be removed prior to use. Multiple sheets or strips can be packaged together in a box or other packaging.

As described above, the compositions and articles described herein comprise a metal salt comprising a metal ion having antimicrobial efficacy, for example, silver ion or copper ion. Dissociable ionic compounds capable of providing the metal ion are well known. The amount of the compound and ion can be accommodated to address the size of the wash basins and laundry loads. An amount of silver ion imparted to the textiles at the end of the laundry process to provide an antimicrobial effect is within the range of about 1 milligram per kilogram of textile (mg/kg) to about 100 mg/kg. For example, in some embodiments, the amount of silver ion imparted to the textiles at the end of the laundry process is within the range of about 1 mg/kg to about 90 mg/kg, or about 1 mg/kg to about 80 mg/kg, or about 1 mg/kg to about 70 mg/kg, or about 1 mg/kg to about 60 mg/kg, or about 1 mg/kg to about 50 mg/kg, or about 1 mg/kg to about 40 mg/kg, or about 1 mg/kg to about 30 mg/kg, or about 5 mg/kg to about 100 mg/kg, or about 10 mg/kg to about 100 mg/kg, or about 20 mg/kg to about 100 mg/kg, or about 30 mg/kg to about 100 mg/kg, or about 40 mg/kg to about 100 mg/kg, or about 50 mg/kg to about 100 mg/kg, or about 60 mg/kg to about 100 mg/kg, or about 70 mg/kg to about 100 mg/kg, or about 2 mg/kg to about 90 mg/kg, or about 3 mg/kg to about 80 mg/kg, or about 4 mg/kg to about 70 mg/kg, or about 5 mg/kg to about 60 mg/kg, or about 6 mg/kg to about 50 mg/kg, or about 7 mg/kg to about 40 mg/kg. The efficiency of the transfer of the ion to the textile will affect the necessary amount of ion in the composition or article.

Accordingly, in various embodiments the amount of metal ion can be in the range of about 10 to about 100 mg/kg, depending on the anticipated size of a laundry load. As one example, in a typical household washer having a laundry basin holding about 10 to 20 L of water and a laundry load of about 10 kg of textiles, an amount of silver nitrate in the composition or article could range from about 16 mg to about 316 mg, which contains about 10 mg to about 200 mg of silver ion. For example, in some embodiments, the amount of silver ion in the composition or article is within the range of about 10 mg to about 180 mg, or about 10 mg to about 160 mg, or about 10 mg to about 140 mg, or about 10 mg to about 120 mg, or about 10 mg to about 100 mg, or about 10 mg to about 80 mg, or about 10 mg to about 60 mg, or about 20 mg to about 200 mg, or about 40 mg to about 200 mg, or about 60 mg to about 200 mg, or about 80 mg to about 200 mg, or about 100 mg to about 200 mg, or about 120 mg to about 200 mg, or about 140 mg to about 200 mg, or about 20 mg to about 180 mg, or about 40 mg to about 160 mg, or about 60 mg to about 140 mg. The amount of silver salt can be adjusted to address variations in, for example, the size of a wash basin and/or laundry load, and/or to accommodate a desired release profile. Similar amounts can be used for other metallic ionic compounds to provide metal ion in an amount that provides antimicrobial efficacy to a treated textile.

In one embodiment where the metal salt is silver nitrate, impregnated into a sheet or strip, the amount of silver nitrate could range from about 16-316 mg, which contains about 10-200 mg silver ion. This amount of silver ion would be sufficient to treat about 10 kg of laundry in a laundry basin of about 10-20 L. In addition, the amount of silver nitrate in the gel coating may range from about 0 mg to about 300 mg, depending on the amount of silver nitrate impregnated onto the sheet, and whether a water-soluble outer later is included. If the outer layer is included, about 0 mg to about 300 mg of silver nitrate can be included between the outer layer and the gel-coated strip or sheet.

When dissolved, the metal salts provide metal ions, such as silver or copper ions, to a wash basin, which will bind with the fabric in the laundry. In one embodiment, the second salt is present to reduce the concentration of the metal ion in the wash water so that it is less concentrated and less toxic. For instance, the second salt may have "binding" properties that limit the availability of free metal ions in solution by providing counterions with which metal ions have a low dissociation constant. Because the counterion binds the metal ion, the second salt can control the rate of release of the metal ions. In some embodiments, a majority of the metal ions are prevented from being released early in the wash cycle. Because of some metals ions', such as silver ions', strong attraction for fabric, the rate of ion release into a wash cycle may be controlled to prevent inconsistent distribution of the metal ion throughout a laundry load that may result from a particle's complete dose of the metal ion becoming immediately available and adhered to fabrics in the immediate vicinity of the particle in the laundry load.

A variety of compounds may be suitable for use as the second salt in accordance with the articles and compositions of the disclosure. Examples that may be suitable for the second salt are shown in Table 1, which provides a non-exclusive list of useful compounds that are arranged in descending order of dissociation constant between silver ion and the counterion of the second salt. In general, the lower the dissociation constant, the lower the concentration of available silver ion in solution (i.e., solubility). For example, compounds such as sodium nitrate and sodium fluoride can be mixed with silver nitrate to reduce the total amount of silver in the core composition. As shown in Table 1, this composition would be the quickest to dissociate and make silver ion available in the wash bath. In other examples, mixture with compounds such as sodium chloride and sodium sulfate will provide counterions (e.g., $Cl^-$, $SO_4^{2-}$) that will more strongly associate with silver, limiting the concentration of available silver ion in the wash bath. In such examples, as available silver ion is removed from solution (e.g., through deposition onto clothing or textile), more silver will dissociate from the second counterion and become available as silver ion.

TABLE 1

| Binder | Binding Ion | Dissociation Constant | Silver Ion Availability | Counter-ion formula | Solubility Limit (g/100 mL) |
|---|---|---|---|---|---|
| Sodium Nitrate | Nitrate | ↑ | ↓ | $AgNo_3$ | 256 |
| Sodium Fluoride | Fluoride | | | AgF | 100 |
| Potassium Sulfate, Sodium Sulfate | Sulfate | | | $Ag_2SO_4$ | 0.83 |
| Sodium Carbonate | Carbonate | | | $Ag_2CO_3$ | 0.0032 |
| Sodium Chloride | Chloride | | | AgCl | 1.60E−04 |
| Sodium Sulfide | Sulfide | | | $Ag_2S$ | 6.21E−16 |

Sodium sulfate is already used as a filler in powdered laundry detergents, so its safety and efficacy is well established. In addition to the compounds shown in Table 1, compounds that provide other ions, such as bromide and iodide ions, may be used (e.g., sodium or potassium bromide or iodide). In various embodiments, the dissociation constant of the metal ion and the first counterion is equal to or greater than the dissociation constant of the metal ion and the second counterion.

An example of how the ion exchange process might work with silver nitrate as the metal salt and sodium sulfate as the second salt is presented below:

1)

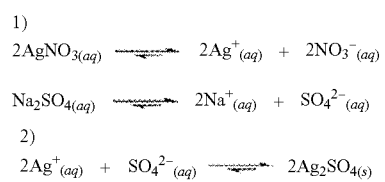

2)

In the first step, silver nitrate ($AgNO_3$) and sodium sulfate ($Na_2SO_4$) could be provided in a composition (e.g., impregnated into or enclosed by particles, or included between a gel-coated strip or sheet and a water-soluble outer layer). Once the compounds are in the presence of wash water, a solution containing ions of silver ($Ag^+$), sodium ($Na^+$), nitrate ($NO_3^-$) and sulfate ($SO_4^{2-}$) is formed. In a second step, silver and sulfate ions strongly associate to form silver sulfate ($Ag_2SO_4$), limiting the availability of silver ions in solution. When silver sulfate is in the presence of the wash water, silver and sulfate ions will slowly dissociate and be released into the wash bath. As silver ions are deposited onto the clothing or textiles, more silver will dissociate from sulfate, becoming available as silver ions. Alternatively, silver (from silver sulfate) can come into contact with and be deposited directly onto clothing or textiles, e.g., in a dryer.

Alternatively, silver sulfate may be substituted for the two ingredients, silver nitrate and sodium sulfate, before being impregnated into or enclosed by particles, or included between a gel-coated strip or sheet and a water-soluble outer layer. This same substitution option applies to all of the other compounds listed in Table 1. The difference is that only the second step, above, would occur in the presence of the wash water.

Similarly, sodium carbonate and potassium sulfate will form silver compounds that are less soluble than silver nitrate. The chemical process for these two compounds with silver nitrate are shown below:

Sodium Carbonate

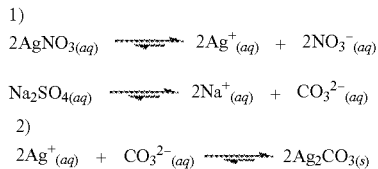

Potassium Sulfate

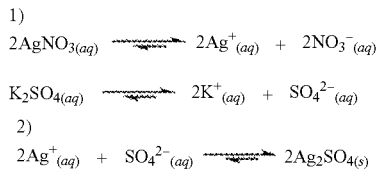

Various aspects of the disclosure are directed to methods for introducing a metal ion to a wash cycle and/or a rinse cycle, for example, to treat a textile. In some embodiments, the method includes dispensing, at or near the beginning of the wash cycle, a composition of the particles as described herein. In one embodiment, metal ion is released from particles at differing rates, depending on particle size, contents and material, over time during the wash and/or rinse cycle, in order to ensure a uniform deposition of metal ion onto laundry fabrics. For instance, the ion is released from the plurality of particles having at different sizes, different amounts of silver ion impregnated or encapsulated therein, and/or a plurality different materials with varying dissolution properties. Therefore, over the course of the wash cycle and rinse cycle or either cycle alone, the metal ion will be released into the wash basin. In some embodiments, the particles may completely dissolve by the time the final rinse and spin cycle is completed.

The composition of the metal-salt-impregnated water-soluble particles can be dispensed into the washing machine drum with the laundry by the user. The composition can be packaged in a box or other container along with a measuring cup to aid the user in adding the proper quantity of the composition to the washing machine drum. The composition may also be contained in liquid or dry form in a dissolvable outer covering similar to a laundry pod or in the form of a gel carrier. The pod or gel carrier may have two or more compartments that dissolve at different rates, releasing the particles at different times during the wash and rinse cycle. Materials for laundry pods are well known and include the water-soluble polymers described herein.

In another example, in some embodiments, the method includes loading a textile into a wash basin containing water, and loading into the wash basin an article as described herein. In some embodiments, the method includes washing the textile in a wash basin in the presence of an article comprising a sheet or strip, as described herein, transferring the textile and article from the wash basin to a dryer, and drying the textile in the presence of the article.

The invention claimed is:

1. An article for imparting antimicrobial efficacy to a textile, the article comprising
a sheet or strip impregnated with a dissolvable metal salt selected from silver sulfate, silver nitrate, silver chloride, and any mixture thereof, wherein the metal salt dissolves to form silver ions, wherein the silver ions have a first release rate from the sheet or strip; and
coated onto the sheet or strip, a gel consisting of a dissolvable layer having a first thickness and a dissolvable metal salt selected from silver sulfate, silver nitrate, silver chloride, and any mixture thereof, wherein the metal salt dissolves to form silver ions, wherein the silver ions have a second release rate from the gel, and wherein the second release rate is controlled by the dissolvable layer.

2. The article of claim 1, wherein
the strip or sheet is folded; and
the gel is coated onto the folded strip or sheet.

3. The article of claim 1, wherein the sheet or strip is impregnated with a second salt comprising nitrate, fluoride, sulfate, carbonate, chloride, bromide, iodide, or sulfide.

4. The article of claim 3, wherein the second salt is selected from sodium sulfate, potassium sulfate, sodium carbonate, and any mixture thereof.

5. The article of claim 1, wherein the dissolvable layer comprises polyvinyl alcohol, a polyacrylamide, poly(acrylic acid), poly(dimethylaminoethylacrylate), poly(dimethylacrylamide), polyethylene glycol, ethyl cellulose, gelatin, or sodium alginate.

6. The article of claim 1, wherein the sheet or strip is further impregnated with copper sulfate, copper chloride, copper nitrate, or silver acetate.

7. A method for introducing a metal ion to at least one of a wash cycle and a rinse cycle, comprising
dispensing, at or near the beginning of the wash cycle, an article for imparting antimicrobial efficacy to a textile, the article comprising:
a sheet or strip impregnated with a dissolvable metal salt selected from silver sulfate, silver nitrate, silver chloride, and any mixture thereof, wherein the metal salt dissolves to form silver ions, wherein the silver ions have a first release rate from the sheet or strip; and
coated onto the sheet or strip, a gel consisting of a dissolvable layer having a first thickness and a dissolvable metal salt selected from silver sulfate, silver nitrate, silver chloride, and any mixture thereof, wherein the metal salt dissolves to form silver ions, wherein the silver ions have a second release rate from the gel, and wherein the second release rate is controlled by the dissolvable layer.

8. A method for treating a textile, comprising
loading the textile into a wash basin containing water; and
loading the article of claim 1 into the wash basin.

9. A method for treating a textile, comprising
washing the textile in a wash basin in the presence of the article of claim 1;
transferring the textile and article from the wash basin to a dryer; and
drying the textile in the presence of the article.

\* \* \* \* \*